United States Patent [19]

Hort et al.

[11] 4,276,215

[45] Jun. 30, 1981

[54] PURIFICATION OF PYRROLIDONE

[75] Inventors: Eugene V. Hort, Wayne; Waldo R. De Thomas, Parsippany, both of N.J.

[73] Assignee: GAF Corporation, New York, N.Y.

[21] Appl. No.: 818,564

[22] Filed: Jul. 25, 1977

[51] Int. Cl.³ .......................................... C07D 201/16
[52] U.S. Cl. .......................................... 260/326.5 FN
[58] Field of Search ................ 260/326.5 J, 326.5 FM

[56] References Cited

U.S. PATENT DOCUMENTS

| 2,667,483 | 1/1954 | Zeegers | 260/326.5 FN |
| 2,828,307 | 3/1958 | Soeterbrock et al. | 260/326.5 FN |
| 3,701,814 | 10/1972 | Shilling | 260/326.5 FN |
| 3,969,344 | 7/1976 | Ackermann et al. | 260/326.5 FN |

FOREIGN PATENT DOCUMENTS

| 2305921 | 8/1973 | Fed. Rep. of Germany | 260/326.5 FN |
| 1092630 | 11/1967 | United Kingdom | 260/326.5 FN |
| 1398501 | 6/1973 | United Kingdom | 260/283 SY |

OTHER PUBLICATIONS

Merck Index, 8th Ed., p. 194, Merck & Co., Rahway, N.J., 1968.

*Primary Examiner*—Donald G. Daus
*Assistant Examiner*—D. B. Springer
*Attorney, Agent, or Firm*—James Magee, Jr.; Walter Katz

[57] ABSTRACT

2-Pyrrolidone is purified by contact with particulate calcium oxide for a sufficient time at elevated temperatures followed by distilling and condensing the purified 2-pyrrolidone.

8 Claims, No Drawings

PURIFICATION OF PYRROLIDONE

This invention relates to a new process for the purification of 2-pyrrolidone, and more particularly to a method of reducing the amount of or eliminating gamma-butyrolactone and pyrrolinyl-pyrrolidone impurities therein. Although 2-pyrrolidone can be produced by several different methods, for example from gamma-aminobutyric acid, from succinimide, from gamma-hydroxybutyramide, etc., its commerical method of production is considered to involve the reaction of gamma-butyrolactone with ammonia. The resulting commercial 2-pyrrolidone generally contains endogenous substances or impurities which may be inert or may act as inhibitors or activators in a subsequent polymerization of the 2-pyrrolidone. Generally, the commercial 2-pyrrolidone contains about 0.5 to 1.5% impurities which may include about 0.03 to 0.2% of unreacted gamma-butyrolactone and about 0.1 to 0.4% of pyrrolinylpyrrolidone in addition to varying amounts of water, methylpyrrolidones, ammonia, pyrrole, amides, amino acids, tetrahydrofuran and the like.

Among its many uses, 2-pyrrolidone can be homopolymerized to produce a useful high molecular weight thermoplastic product commonly referred to as polypyrrolidone or nylon-4. According to a known method, the polymerization can be carried out in the presence of alkaline polymerization catalysts such as potassium hydroxide, potassium pyrrolidone and the like. According to another known procedure the activity of these catalysts during the polymerization with reference to the rate of the polymerization, yield and quality of the polymer, etc. can be enhanced by the addition thereto of various compounds classed as polymerization activators.

It is well recognized that in order to prepare a polymer from 2-pyrrolidone suitable for preparing commercially acceptable products such as fibers, filaments, and other shaped objects, the impurities in the 2-pyrrolidone must be sufficiently reduced in amount or eliminated. Impurities or endogenous substances known to inhibit polymerization will by definition prevent optimal polymerization for the production of high quality, high molecular weight polypyrrolidone. Endogenous activators such as gamma-butyrolactone and pyrrolinyl-pyrrolidone should likewise be minimized or eliminated since their proportions in the commercial 2-pyrrolidone vary from batch to batch, activator concentration in the polymerization medium varies inversely with the ultimate molecular weight of the polypyrrolidone product, and it is accordingly necessary to maintain control of the activator concentration to very close tolerances in order to obtain a high quality, high molecular weight polymer.

A number of methods have heretofore been proposed for the purification of 2-pyrrolidone. Thus, U.S. Pat. No. 2,802,777 describes crystallization of 2-pyrrolidone as the hydrate followed by drying, as by azeotropic distillation and distillation in vacuo. U.S. Pat. No. 2,806,856 discloses successive distillation of 2-pyrrolidone from an acid anhydride and a base. U.S. Pat. No. 3,026,301 mentions fractional distillation from KOH solution. U.S. Pat. No. 3,033,831 mentions conventional crystallization procedures. U.S. Pat. No. 3,184,476 describes several alternative procedures including acidic treatment with phosphorus pentoxide or sulfuric acid, anhydrous distillations, etc., and recommends treatment of the 2-pyrrolidone with water at elevated temperatures to hydrolyze the pyrrolinylpyrrolidone to 2-pyrrolidone. U.S. Pat. No. 3,681,293 describes distillation under vacuum through a wiped film evaporator. British No. 1,398,501 describes a substantially anhydrous procedure involving flash distilling a solution of alkali metal or alkaline earth metal hydroxide in the 2-pyrrolidone through a molecular still.

None of these previously proposed purification procedures are entirely satisfactory from the viewpoint of cost, efficiency, ease of control, rapidity, and/or quality of monomer, and/or quality and molecular weight of polymer obtained therefrom. Further, substantially few if any such procedures are effective to remove both endogenous inhibitors, and endogenous activators such as pyrrolinyl-pyrrolidone which in fact is actually increased in amount by procedures conducted under prolonged anhydrous conditions and/or elevated temperatures, i.e. dehydrating conditions.

It is an object of this invention to provide a purification process which will not be subject to one or more of the above disadvantages. Another object of the invention is the provision of such a process effective to remove gamma-butyrolactone from commercial 2-pyrrolidone and convert pyrrolinyl-pyrrolidone therein to 2-pyrrolidone. Still another object of the invention is the provision of such a process which results in a purified 2-pyrrolidone polymerizable at satisfactory rates with high yields of high molecular weight polypyrrolidone. Other objects and advantages will appear as the description proceeds.

The attainment of one or more of the above objects is made possible by this invention which includes a process for removing impurities from 2-pyrrolidone comprising continuously passing the impure liquid 2-pyrrolidone through a zone containing calcium oxide in particulate form, said zone being maintained at a temperature of about 80° to 250° C. and the average residence time of the pyrrolidone in said zone ranging from about 5 minutes to 10 hours, rapidly distilling the effluent calcium salt-containing 2-pyrrolidone, and condensing the purified 2-pyrrolidone.

The process of this invention has been found to be relatively lower in cost and more readily controlled, and to yield a higher quality purified 2-pyrrolidone monomer polymerizable to higher yields of better quality, higher molecular weight polypyrrolidone at satisfactory rates. The mechanism by which the present process operates is not well understood, since other alkaline earth metal oxides, i.e. magnesium oxide and barium oxide, when substituted for the essential calcium oxide employed herein, fail to yield acceptable results.

In carrying out the present process, the calcium oxide particles are desirably charged into a tubular vessel which may be maintained horizontal but preferably vertical. The particles are preferably confined in the vessel in a zone bounded at one or both ends by perforated plates, screens, grates or the like. The liquid commercial 2-pyrrolidone to be purified is fed or pumped through the tubular vessel in either direction, preferably into the bottom of a vertically maintained vessel in which it flows upward through the calcium oxide particles at a rate (i.e. residence time) necessary to yield the desired purified 2-pyrrolidone. Such rate generally calls for an average residence time of the influent 2-pyrrolidone in said zone containing the calcium oxide particles ranging from about 5 minutes to 10 hours, usually about 10 minutes to 5 hours, depending upon the amount and type of the endogenous substances in the influent liquid.

The treatment of the 2-pyrrolidone with the calcium oxide particles is carried out at elevated temperatures of about 80° to 250° C., preferably about 140° to 200° C., involving heating said zone and the calcium oxide particles and preferably the influent 2-pyrrolidone and the tubular vessel itself. At higher temperatures within the aforementioned ranges, a shorter contact or residence time, i.e. a higher rate of flow, may be employed to yield the desired results, it being understood that too high a temperature tends to decompose and produce further impurities in the 2-pyrrolidone. On the other hand, inadequate purification takes place if the temperature is too low.

The calcium oxide particles have an average diameter ranging from about 0.5 to 12, preferably about 3 to 7, mm., in any regular or irregular surface configuration or shape such as granules, pebbles, marbles, lumps, and the like, and rest in said zone in what might be termed a bed; i.e. fixed, fluid or jiggling depending on the shape, size and size distribution of the particles, the free space in the bed, the length or height of the bed, the rate of flow of the commercial 2-pyrrolidone therethrough, and the like. It will be understood that these factors, and the treatment temperature, are interrelated and interdependent in determining optimal conditions for the desired purification.

As the flow of 2-pyrrolidone through the zone containing the calcium oxide particles proceeds, the particles gradually dissolve to form calcium salts or complexes in the 2-pyrrolidone. The particles may be permitted to completely dissolve whereafter the process is continued with a new supply of calcium oxide charged into said zone, or the process may be extended or made more continuous and uninterrupted by continuously or intermittently replenishing the bed of calcium oxide particles, as by charging fresh particles into the upper end of said zone in the vertically positioned tubular vessel.

Fixed, jiggling, moving and fluidized beds are described in C. L. Thomas, "Catalytic Processes and Proven Catalysts", Academic Press, New York (1970), pp. 3–9.

The above-described treatment procedure is substantially independent of pressure and is accordingly preferably conducted at atmospheric pressure, although super- or sub-atmospheric pressures may be desirable under certain conditions. Similarly, air need not, though preferably is, excluded, as by purging with nitrogen or the like.

Following treatment with the calcium oxide particles, the effluent 2-pyrrolidone containing dissolved calcium salt impurities must be stripped or distilled to separate out such impurities. Rapid distillation under reduced pressure is required to minimize further formation of pyrrolinyl-pyrrolidone from the 2-pyrrolidone being purified. This is preferably accomplished by flash distillation of the effluent 2-pyrrolidone, either intermittently or continuously, under reduced pressure below about 20 mm. Hg, down to about 1 mm. Hg. or less, use of a wiped film evaporator or molecular still being particularly suitable for this purpose. The condensed 2-pyrrolidone from this distillation is in a highly purified state containing less than about 0.03% of each of butyrolactone and pyrrolinyl-pyrrolidone.

The following examples are only illustrative and not limitative of this invention. All amounts and proportions referred to herein and in the appended claims are by weight unless otherwise indicated. The commercial 2-pyrrolidone feed in these examples contains 0.105% of gamma-butyrolactone and 0.19% of pyrrolinyl-pyrrolidone.

EXAMPLE 1

A pyrex glass tube with an internal diameter of 1 inch and a length of 12 inches is packed with 30 ml. of calcium oxide granules having an average diameter of about 3–7 mm. To the bottom of the tube is attached a feed pump and a burette containing the feed, a commercial grade 2-pyrrolidone. The glass tube containing the calcium oxide and the inlet lines from the feed pump are heated to 165° C. A nitrogen gas purge is used on the exit end of the tube to exclude oxygen. 2-Pyrrolidone is passed upward through the heated bed containing about 75% free space (volume) at a residence time averaging about 15 to 20 minutes. The CaO bed dissolves slowly during the treatment and after 100 volumes of feed per volume of CaO has been treated, the bed is completely dissolved. The treated effluent 2-pyrrolidone is totally stripped through a flash still at 1 mm. Hg. of pressure to give a 97–98% wgt. yield of 2-pyrrolidone containing 0.006% of gamma-butyrolactone, no pyrrolinyl-pyrrolidone, and a 2–3% distillation residue. Polymerization of this product gives high yields of polymer of high molecular weight at a satisfactory rate.

EXAMPLE 2

The same procedure as in Example 1 is employed, but the 2-pyrrolidone feed is heated to 180° C. and passed through the calcium oxide bed at an average residence time of 12 to 15 minutes. The CaO bed dissolves after 100 volumes of feed per volume of CaO has been treated. The treated effluent 2-pyrrolidone is totally stripped through a flash still at 1 mm. Hg. pressure to give 97–98% wgt. yield of 2-pyrrolidone approximating the quality of the product of Example 1. Polymerization of this product gives high yields of polymer of high molecular weight at a satisfactory rate.

EXAMPLE 3

The same procedure as in Example 1 is employed but the 2-pyrrolidone feed is heated to 150° C. and passed through the calcium oxide bed at an average residence time of 60 to 70 minutes. The CaO bed dissolves after 100 volumes of feed per volume of CaO has been treated. The treated effluent 2-pyrrolidone is totally stripped through a flash still at 1 mm. Hg. pressure, with results similar to those of the previous examples.

This invention has been disclosed with respect to certain preferred embodiments and it will be understood that modifications and variations thereof obvious to those skilled in the art are to be included within the spirit and purview of this application and the scope of the appended claims.

What is claimed is:

1. A process for removing impurities from 2-pyrrolidone comprising the steps of continuously passing the impure liquid 2-pyrrolidone through a zone containing calcium oxide in particulate form, said zone being maintained at a temperature of about 80° to 250° C. and the average residence time of the pyrrolidone in said zone ranging from about 5 minutes to 10 hours, rapidly distilling the effluent calcium salt-containing 2-pyrrolidone, and condensing the purified 2-pyrrolidone.

2. A process as defined in claim 1 wherein said temperature ranges from about 140° to 200° C. and said average residence time ranges from about 10 minutes to 5 hours.

3. A process as defined in claim 1 wherein the calcium oxide particles have an average diameter ranging from about 0.5 to 12 mm.

4. A process as defined in claim 1 wherein the calcium oxide particles have an average diameter ranging from about 3 to 7 mm.

5. A process as defined in claim 1 wherein said particles are in the form of a fixed, fluid or jiggling bed.

6. A process as defined in claim 1 wherein said effluent 2-pyrrolidone is flash distilled under a reduced pressure below about 20 mm. Hg.

7. A process as defined in claim 6 wherein said particles have average diameters ranging from about 3 to 7 mm. and are in the form of a fixed, fluid or jiggling bed.

8. A process as defined in claim 7 wherein said flash distillation is carried out in a wiped film evaporator.

* * * * *